(12) United States Patent
Miller (10) Patent No.: US 8,979,895 B2
(45) Date of Patent: Mar. 17, 2015

(54) METHOD AND APPARATUS OF ENDOSCOPIC SUTURING

(75) Inventor: Larry S. Miller, Bala Cynwyd, PA (US)

(73) Assignee: Temple University—of the Commonwelth System of Higher Education, Philadelphia, PA (US)

( * ) Notice: Subject to any disclaimer, the term of this patent is extended or adjusted under 35 U.S.C. 154(b) by 2170 days.

(21) Appl. No.: 11/665,587

(22) PCT Filed: Oct. 18, 2005

(86) PCT No.: PCT/US2005/037329
§ 371 (c)(1),
(2), (4) Date: Oct. 27, 2009

(87) PCT Pub. No.: WO2006/044837
PCT Pub. Date: Apr. 27, 2006

(65) Prior Publication Data
US 2010/0036395 A1    Feb. 11, 2010

Related U.S. Application Data

(60) Provisional application No. 60/619,766, filed on Oct. 18, 2004.

(51) Int. Cl.
*A61B 17/04* (2006.01)
*A61B 17/06* (2006.01)

(52) U.S. Cl.
CPC ......... *A61B 17/0401* (2013.01); *A61B 17/0487* (2013.01); *A61B 17/0469* (2013.01);
(Continued)

(58) Field of Classification Search
USPC .................................. 606/139, 213, 232, 228
See application file for complete search history.

(56) References Cited

U.S. PATENT DOCUMENTS 4,235,238 A * 11/1980 Ogiu et al. .................... 606/145
5,085,661 A    2/1992 Moss
(Continued)

FOREIGN PATENT DOCUMENTS

EP    0643945 A1    3/1995
WO    WO01/54585 A1    8/2001
(Continued)

*Primary Examiner* — Dianne Dornbusch
(74) *Attorney, Agent, or Firm* — Drinker Biddle & Reath LLP (57) ABSTRACT

An adjustable suture assembly is provided that may be employed in various surgical procedures to draw and/or hold tissue and/or muscle together. The suture assembly may include a suture lock or tensioner that is adjustably securable to two or more lengths of suture to provide a surgeon with an ability to maintain tissue or muscle in one secured position and subsequently readjust the suture assembly to maintain the tissue or muscle in a different secured position. The suture assembly may include two or more sutures having an anchor attached to an end of each suture for anchoring the suture to desired tissue or muscle. An endoscopic suturing device is provided to deliver and place two or more sutures in tissue or muscle during a surgical procedure. The suturing device may be configured to carry a plurality of sutures so that multiple sutures can be placed in tissue or muscle during a single intubation of the device. The suture assembly and suturing device may be employed with an endoscope to facilitate surgical treatment of obesity which involves narrowing and/or disabling the pyloric sphincter to reduce the rate of gastric emptying.

9 Claims, 5 Drawing Sheets

(52) U.S. Cl.
CPC . *A61B2017/0409* (2013.01); *A61B 2017/0417* (2013.01); *A61B 2017/0445* (2013.01); *A61B 2017/0458* (2013.01); *A61B 2017/0461* (2013.01); *A61B 2017/0464* (2013.01); *A61B 2017/0488* (2013.01); *A61B 2017/06052* (2013.01)
USPC .......................................... 606/232; 606/139

(56) References Cited

U.S. PATENT DOCUMENTS

| | | | |
|---|---|---|---|
| 5,269,809 A | 12/1993 | Hayhurst et al. | |
| 5,383,905 A | 1/1995 | Golds et al. | |
| 5,417,691 A * | 5/1995 | Hayhurst ...................... | 606/232 |
| 5,445,167 A | 8/1995 | Yoon et al. | |
| 5,466,241 A | 11/1995 | Leroy et al. | |
| 5,562,689 A | 10/1996 | Green et al. | |
| 5,626,614 A | 5/1997 | Hart | |
| 5,683,417 A | 11/1997 | Cooper | |
| 5,948,000 A | 9/1999 | Larsen et al. | |
| 6,010,525 A * | 1/2000 | Bonutti et al. ................ | 606/232 |
| 6,056,760 A * | 5/2000 | Koike et al. ................... | 606/148 |
| 6,066,160 A * | 5/2000 | Colvin et al. .................. | 606/232 |
| 6,174,323 B1 | 1/2001 | Biggs et al. | |
| 6,319,263 B1 | 11/2001 | Levinson | |
| 6,500,184 B1 * | 12/2002 | Chan et al. .................... | 606/144 |
| 6,540,789 B1 | 4/2003 | Silverman et al. | |
| 6,558,400 B2 | 5/2003 | Deem et al. | |
| 7,431,726 B2 * | 10/2008 | Spence et al. ................. | 606/151 |
| 7,737,109 B2 | 6/2010 | Miller | |
| 2001/0023352 A1 | 9/2001 | Gordon et al. | |
| 2001/0041916 A1 * | 11/2001 | Bonutti ......................... | 606/232 |
| 2001/0044639 A1 | 11/2001 | Levinson | |
| 2003/0093117 A1 * | 5/2003 | Saadat ........................... | 606/221 |
| 2003/0236535 A1 * | 12/2003 | Onuki et al. .................. | 606/144 |
| 2004/0092969 A1 * | 5/2004 | Kumar ........................... | 606/151 |
| 2004/0147958 A1 | 7/2004 | Lam et al. | |
| 2004/0153074 A1 | 8/2004 | Bojarski et al. | |
| 2004/0167546 A1 | 8/2004 | Saadat et al. | |
| 2005/0187577 A1 * | 8/2005 | Selvitelli et al. .............. | 606/232 |

FOREIGN PATENT DOCUMENTS

| | | |
|---|---|---|
| WO | WO03/001893 A2 | 1/2003 |
| WO | WO03/007772 A1 | 9/2003 |
| WO | WO2006/044837 A3 | 4/2006 |

* cited by examiner

METHOD AND APPARATUS OF ENDOSCOPIC SUTURING

FIELD OF THE INVENTION

The present invention relates to an apparatus for performing endoscopic procedures. More particularly, the invention relates to an adjustable suture assembly and an apparatus adapted for endoscopic placement of sutures.

DISCUSSION OF RELATED ART

U.S. Pat. No. 6,558,400 (Deem) discloses various tools and methods for performing gastroplasty procedures, such as the treatment of obesity. Deem discloses endoscopically applying a plurality of anchors to the gastrointestinal tract wall along the length of the stomach. The anchors are tensioned using a suture received by the anchors to form a reduced pouch within the stomach.

U.S. Pat. No. 5,626,614 (Hart) discloses a suture anchor in the form of a cylindrical tube attached to the end of a suture at an intermediate location along the anchor. This type of anchored suture is sometimes referred to as a "T-anchor" suture in view of the combined shape of the anchor and suture. Hart also discloses an apparatus that includes an elongated needle that is driven through the abdominal wall and the stomach wall to deliver the anchor into the interior of the stomach. The stomach wall is then pulled outwardly by the anchored suture to hold the stomach wall in close proximity to the abdominal wall.

SUMMARY OF THE INVENTION

In one illustrative embodiment of the invention, an adjustable suture assembly comprises a first suture and a first anchor attached to an end of the first suture, a second suture and a second anchor attached to an end of the second suture, and a suture lock to adjustably secure the first and second sutures in a first secured position and subsequently in a second secured position. The first and second anchors are constructed and arranged to anchor the first and second sutures to tissue or muscle.

In another illustrative embodiment of the invention, an endoscopic suturing device comprises an elongated catheter having an axially extending catheter lumen, a needle having an axially extending needle lumen, and a suture assembly including at least first and second anchors and first and second sutures respectively attached to the first and second anchors. Each of the first and second anchors is disposed within the needle lumen, and the needle is slidably disposed within the catheter lumen. The needle includes a distal end that is constructed and arranged to pierce tissue or muscle.

In a further illustrative embodiment of the invention, a method of adjusting the configuration of a hollow body organ is provided. The method comprises acts of (a) placing at least one suture at first and second locations of the hollow body organ with first and second lengths of suture extending, respectively, from the first and second locations; (b) securing the first and second lengths of suture to maintain the first and second locations in a first relative position with the hollow body organ in a first configuration; and (c) following act (b), securing the first and second lengths of suture to maintain the first and second locations in a second relative position with the hollow body organ in a second configuration that is different from the first configuration.

In yet another illustrative embodiment of the invention, a method of adjusting a pyloric sphincter is provided to treat obesity. The method comprises acts of (a) placing at least one suture at first and second locations of the pyloric sphincter with first and second lengths of suture extending, respectively, from the first and second locations; (b) narrowing the pyloric sphincter into a first configuration for reducing gastric emptying; and (c) securing the first and second lengths of suture to maintain the pyloric sphincter in the first configuration.

BRIEF DESCRIPTION OF THE DRAWINGS

Various embodiments of the invention will now be described, by way of example, with reference to the accompanying drawings, in which.

DESCRIPTION OF ILLUSTRATIVE EMBODIMENTS

One aspect of the invention is directed to an adjustable suture assembly that may be employed in various surgical procedures to draw and/or hold tissue and/or muscle together. The suture assembly may include a suture lock or tensioner that is adjustably securable to two or more lengths of suture to provide a surgeon with an ability to maintain tissue or muscle in one secured position and subsequently readjust the suture assembly to maintain the tissue or muscle in a different secured position. In this manner, the suture assembly provides a surgeon with the ability to readily adjust the extent to which the tissue or muscle is held together by the suture so that tissue or muscle may be drawn closer together or allowed to move further apart.

The suture assembly may be particularly suited for endoscopic procedures on hollow body organs, such as the gastrointestinal tract, where two or more portions of the organ may be drawn together to reduce the size or change the shape of the organ. For example, the suture assembly may be used to treat obesity by endoscopically reducing the size of the stomach or forming a reduced gastric pouch, or narrowing the pyloric sphincter to reduce gastric emptying. The suture assembly may also be employed to treat GERD by creating tissue folds or plications in the lower esophageal sphincter (LES) which reduce the size of the LES. The size and/or shape of the hollow body organ may be subsequently changed by adjusting or re-tensioning the suture assembly using the originally placed sutures which may avoid the need to perform the original procedure again.

The suture assembly may include two or more sutures having an anchor attached to an end of each suture for anchoring the suture to desired tissue or muscle. Each anchor may include an elongated body with the suture attached at an intermediate location between the opposing ends of the anchor body. However, the anchor may have any suitable configuration and be attached to the suture in any suitable manner apparent to one of skill in the art.

The suture lock may be configured to be adjustably disposed along each suture. In this regard, the suture lock may be provided with a passage that slidably receives each suture therein. Such an arrangement may allow a surgeon to change the extent to which the tissue or muscle is held together by the sutures by adjusting the position of the suture lock relative to one or more of the sutures and/or anchors. It is to be understood that the suture lock may employ any suitable arrangement apparent to one of skill in the art.

The suture lock and/or sutures may include a securement feature that secures the sutures in a desired state by inhibiting relative movement between the lock and sutures. In one embodiment, each suture may include a securement feature that engages the suture lock and/or each other to inhibit movement therebetween. The securement feature may include a plurality of projections spaced along the length of each suture. However, it is to be appreciated that any suitable securement feature may be provided on the suture anchor and/or sutures as would be apparent to one of skill in the art.

Another aspect of the invention is directed to an endoscopic suturing device that is configured to deliver and place two or more sutures in tissue or muscle during a surgical procedure. The suturing device may be configured to carry a plurality of sutures so that multiple sutures can be placed in tissue or muscle during a single intubation of the device.

The suturing device may include a hollow needle configured to receive suture anchors therein with a suture attached to each anchor. Each anchor may be individually ejected from the needle to anchor its associated suture at a desired location in the tissue or muscle. An elongated slot may be provided along the length of the needle through which the sutures may extend from the needle lumen. A spacer may be disposed in the needle between the anchors to maintain separation between the anchors and thereby limit inadvertent ejection of multiple anchors from the needle during a suturing procedure.

For ease of understanding, and without limiting the scope of the invention, the suture assembly and suturing device are described below particularly in connection with a surgical procedure involving a pyloric sphincter. More particularly, the suture assembly and suturing device may be employed with an endoscope to facilitate surgical treatment of obesity which involves narrowing and/or disabling the pyloric sphincter to reduce the rate of gastric emptying. For example, one or more sutures may be placed into the pyloric sphincter using a suturing device to narrow the sphincter opening. If desired, a medication, drug or bulking agent may also be injected into the pyloric sphincter to stiffen, disable or otherwise alter the function of the muscle. It should be understood, however, that the suture assembly and suturing device are not so limited and may be employed in other surgical procedures as would be apparent to one of skill in the art.

Figure 1:
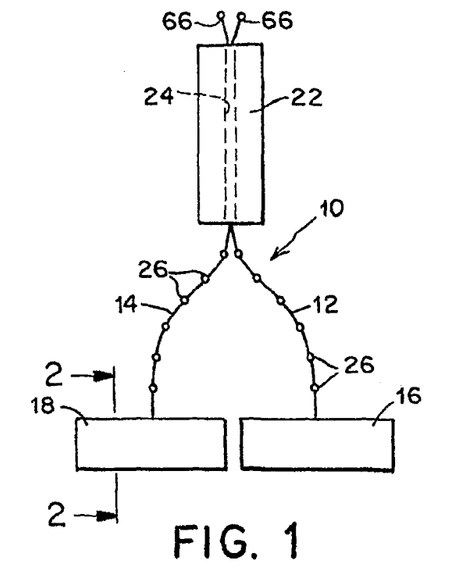
FIG. 1 is a side view of a suture assembly according to one illustrative embodiment of the invention.
Figure 2:
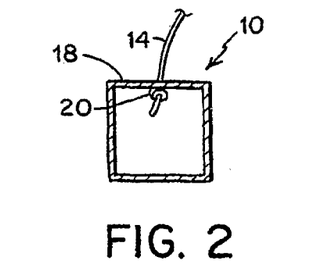
FIG. 2 is a sectional view of one of the anchors of the suture assembly of FIG. 1 taken along the section line 2-2 of FIG. 1.

In one illustrative embodiment shown in FIGS. 1-2, the suture assembly 10 includes first and second sutures 12, 14 respectively attached to first and second anchors 16, 18. However, the suture assembly may include any number of sutures and anchors for performing a particular surgical procedure as would be apparent to one of skill in the art.

Each suture 12, 14 may be attached to the anchor 16, 18 at an intermediate location along the length of the anchor forming anchored sutures of a type known in the art as a "T-anchor" suture. As shown, each suture 12, 14 may be attached to the associated anchor 16, 18 substantially midway between its opposite ends. It is to be understood, however, that the suture need not be attached to an intermediate location of the anchor, but may be attached to any portion of the anchor as would be apparent to one of skill in the art.

As will be described in greater detail below, the anchors 16, 18 of suture assembly 10 may be endoscopically placed through gastrointestinal tissue or muscle to anchor the associated sutures 12, 14 through contact between the anchor 16, 18 and the tissue or muscle.

As shown in FIG. 2, each anchor 16, 18 may include a tubular wall having a substantially square cross-section. However, it is to be appreciated that the anchors may employ any suitable configuration apparent to one of skill in the art. For example, the anchors 16, 18 may be configured to have a rectangular, oval or circular cross section. Additionally, the suture assembly may employ anchors having different configurations on one or more of the sutures if desired for a particular procedure.

As illustrated, an end portion of the suture 12, 14 may be received in an interior of the anchor 16, 18. A knot 20 is formed adjacent the end of the suture to secure the suture to the anchor. As is to be appreciated, however, the anchor may be attached to the suture using any suitable arrangement apparent to one of skill in the art.

The suture assembly 10 also includes a suture lock or tensioner 22 connected to both the first and second sutures 12, 14 of the assembly 10. The suture lock interacts with and secures the sutures in one or more secured positions. The suture lock is configured to be adjustable relative to the sutures so that the suture assembly may be adjusted to vary the degree to which to the tissue or muscle is held together. In one embodiment, the suture lock is slidable relative to the sutures so that a surgeon may adjust the suture assembly by moving the suture lock in both directions along the sutures relative to the anchors to desired positions. In the illustrative embodiment, the suture lock 22 includes a central passage 24 (shown in phantom) extending along its length which slidably receives each suture 12, 14 therethrough.

The suture assembly may include one or more securement features to inhibit relative movement between the sutures and the suture lock and maintain the sutures in a desired secured position. The securement feature may be provided on the suture lock, the sutures or both. In one illustrative embodiment, each of the sutures 12, 14 includes a plurality of projections 26 spaced along a length of the suture. Engagement between the projections 26 and the central passage 24 of the suture lock 22 functions to maintain the lock 22 in a desired location with respect to the sutures 12, 14 and anchors 16, 18 as the lock 22 is advanced along the length of the sutures. The projections on one suture may also interact with the projections on the other suture to inhibit relative movement therebetween. In one embodiment, the projections may include spaced nodules along the length of each suture. It is to be understood that the suture assembly may employ any suitable securement feature apparent to one of skill in the art. For example, the suture-assembly may incorporate detent arrangements, releasable pawl mechanisms or one-way mechanisms, such as those used to hold flexible ties.

Figure 3:
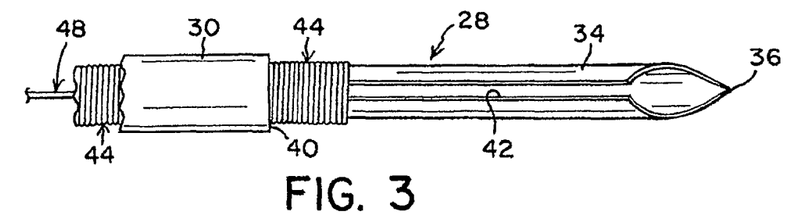
FIG. 3 is a top plan view of an apparatus according to another illustrative embodiment of the invention for endoscopically delivering the suture assembly of FIG. 1.
Figure 4:
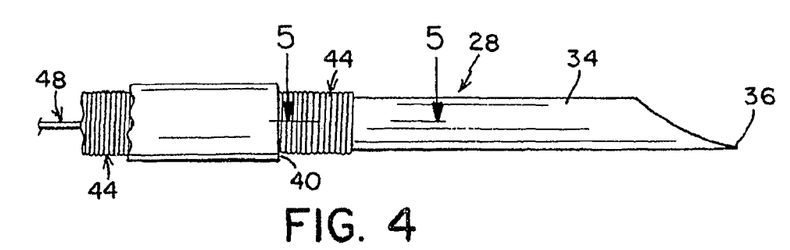
FIG. 4 is a side elevation view of the apparatus of FIG. 3.

The suture assembly may be delivered to and placed in tissue or muscle, such as within the gastrointestinal tract of a patient, using an endoscopic suturing device. In one illustrative embodiment shown in FIGS. 3-6, an endoscopic suturing device 28 includes an elongated needle 34 having a distal end 36 and an opposite proximal end 38 (FIG. 6). The distal end 36 of needle 34 is pointed to facilitate piercing of body tissue or muscle, such as the gastrointestinal tissue or muscle of an individual, by the needle. The pointed distal end 36 may be formed by cutting the needle 34 along curved cut lines as shown in FIGS. 3 and 4.

The needle 34 includes a substantially tubular wall defining a needle lumen adapted to receive the anchors 16, 18 of the suture assembly 10 in a sliding arrangement. As shown in FIG. 3, the needle 34 may include an elongated slot 42 extending longitudinally along the length of the needle 34. The slot 42 is adapted to accommodate the sutures 12, 14 extending between the anchors 16, 18 and the suture lock or tensioner 22, which is located at an exterior location with respect to the needle 34.

The suturing device 28 may include a catheter 30 that is configured to hold the needle and suture assembly. In one embodiment, the catheter 30 includes a substantially cylindrical tube defining a catheter lumen that is adapted to slidably receive the needle 34. As shown in FIGS. 3 and 4, the needle 34 may be extended beyond a terminal end 40 of the catheter 30 in a deployed condition to present the needle 34 for penetration of tissue or muscle.

In one embodiment, the catheter 30 is made from a plastic material to provide for sufficient flexibility for delivery of the catheter 30 into the gastrointestinal tract through a natural body opening such as the mouth. However, it is to be appreciated that the catheter may be fabricated from any suitable material apparent to one of skill in the art. The catheter 30 is preferably adapted for receipt by an endoscope 32 (FIG. 10) within a channel provided by the endoscope for sliding deployment of endoscopic tools from a distal end of the endoscope 32. Endoscopes having working channels for sliding deployment of various surgical and diagnostic tools are known, such that no further description is required.

The suturing device 28 may also include a needle thruster 44 that is slidably received within the catheter 30 and connected to the needle 34. The needle thruster 44 provides for relative movement of the needle 34 with respect to the catheter 30 between a retracted condition (FIG. 7) in which the needle 34 is contained within the lumen of the catheter 30 and a deployed condition (FIGS. 3 and 4). In one illustrative embodiment shown in FIG. 5, the needle thruster 44 is formed by a wire 46 wound in closely spaced coils to form a substantially tubular configuration defining an interior. The wire 46 of the needle thruster 44 may be wrapped about an end portion of the needle 34 to connect the needle thruster 44 to the needle 34. The needle 34 and needle thruster 44 may be further secured to each other by welding or brazing the wire 46 to the needle 34. It is to be understood that the needle thruster may employ any suitable arrangement apparent to one of skill in the art.

The wound-wire construction provides the needle thruster 44 with flexibility to facilitate endoscopic maneuvering of the needle thruster 44 and the attached needle 34 when the suturing device 28 is placed into the gastrointestinal tract of an individual. The wound wire configuration of needle thruster 44, however, also possesses sufficient axial stiffness to provide for driving movement of the needle 34 between the retracted condition (FIG. 7) and the deployed condition. Although only a portion of the needle thruster 44 is seen in the figures, it should be understood that the needle thruster 44 is preferably configured to provide for the desired movement of the needle 34 with respect to the catheter 30 from a remote location outside of the patient.

The suturing device 28 may further include an anchor ejector that is configured to be actuated by a surgeon to eject the anchors from the needle. In one illustrative embodiment, the anchor ejector 48 includes an elongated wire portion 50 and a spring portion 52. Preferably, the spring portion 52 of the anchor ejector 48 is integrally formed with the wire portion 50 by coiling an end portion of a length of wire into the helical configuration shown. However, it is to be understood that the anchor ejector may employ any suitable arrangement apparent to one of skill in the art.

Figure 5:
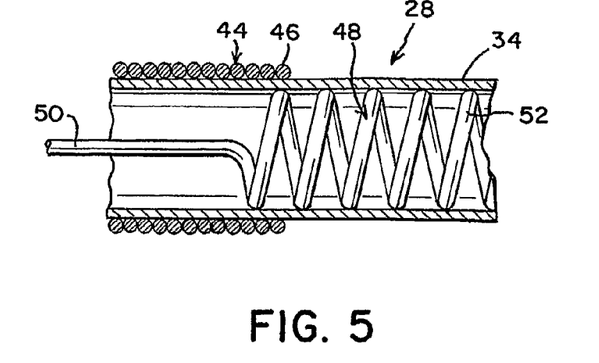
FIG. 5 is a partial sectional view of the apparatus of FIGS. 3 and 4 taken along section line 5-5 of FIG. 3.
Figure 6:
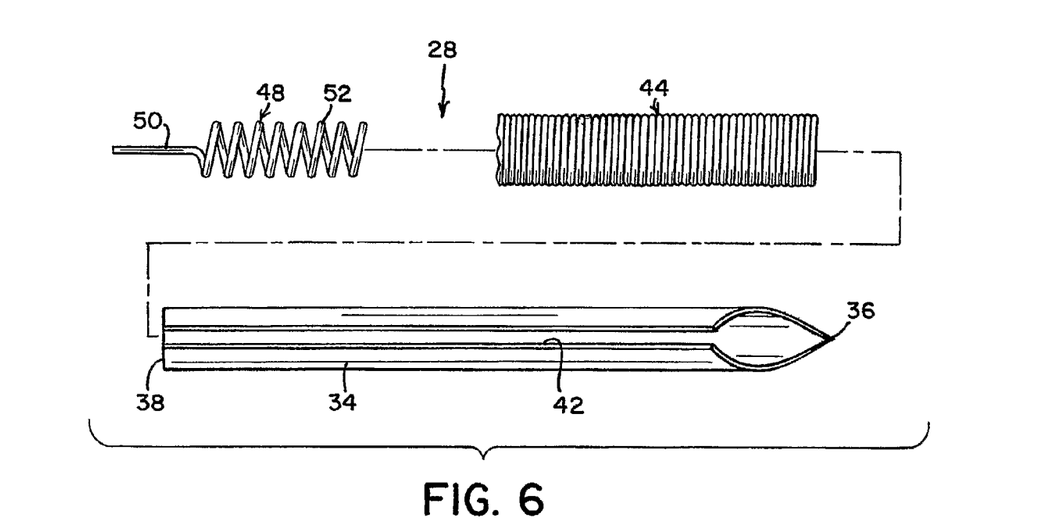
FIG. 6 is an exploded view of a portion of the apparatus of FIGS. 3-5.

As shown in FIG. 5, the spring portion 52 of the anchor ejector 48 is slidably received and within the needle 34. As described below in greater detail, the spring portion 52 of the anchor ejector 48 contacts the anchor of the suture assembly 10 located furthest from the distal end of the needle for ejection of the first and second anchors 16, 18 from the distal end 36 of needle 34.

Figure 7:
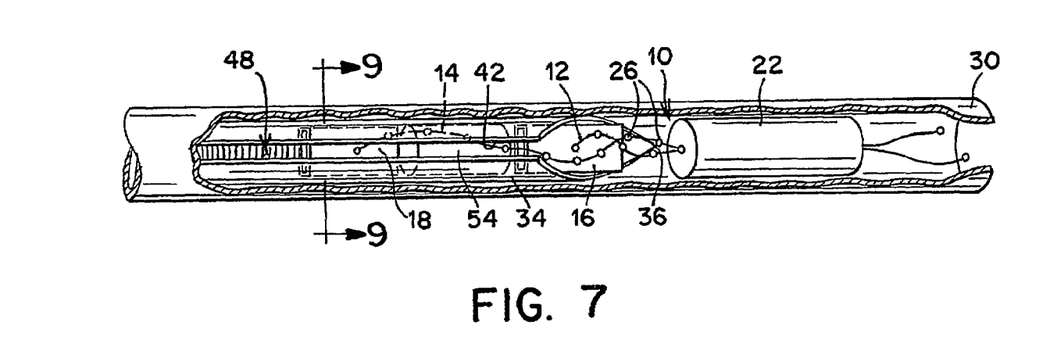
FIG. 7 is a partial top perspective view of the apparatus of FIGS. 3-5 carrying the suture assembly of FIGS. 1-3 with the needle in a retracted condition within the catheter, the needle thruster removed for clarity of view.
Figure 8:
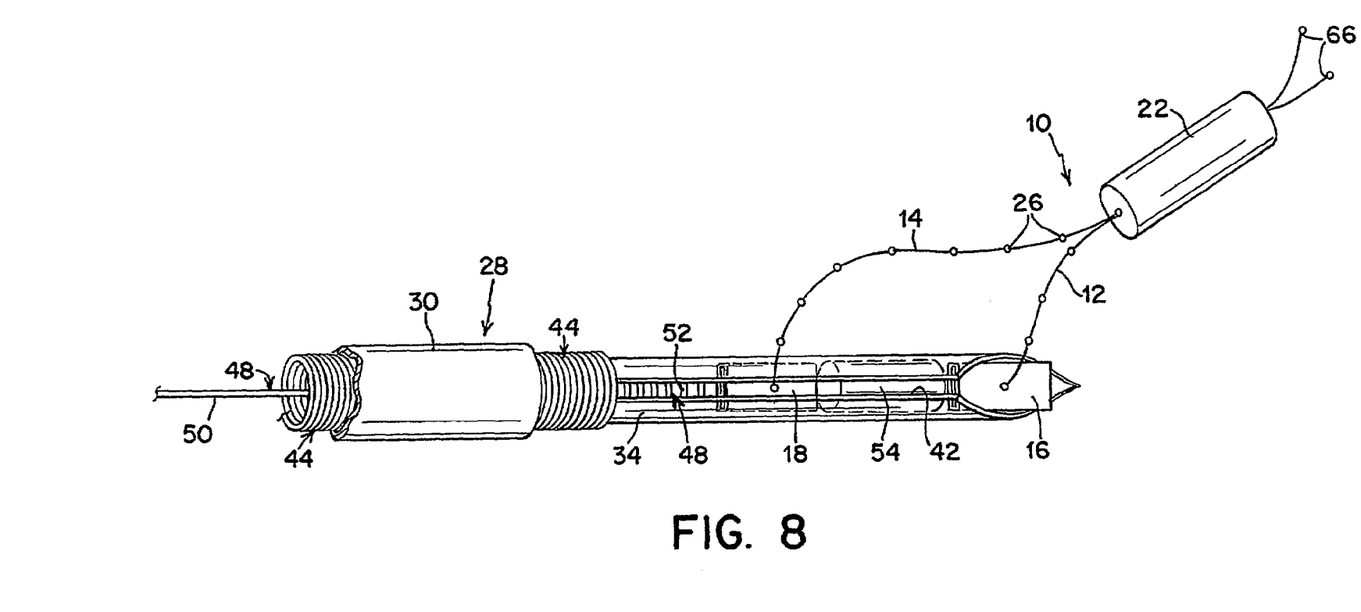
FIG. 8 is a partial top perspective view of the apparatus and suture assembly of FIG. 7 with the needle in a deployed condition.
Figure 9:
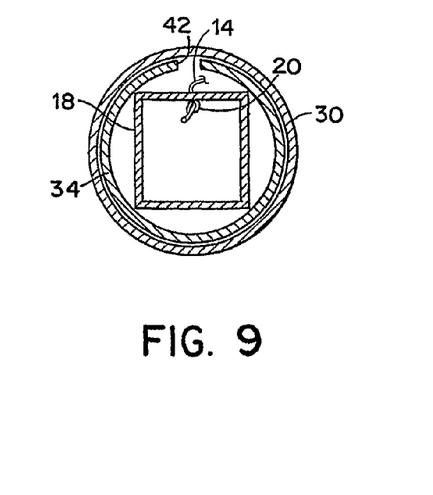
FIG. 9 is a sectional view of the apparatus and suture assembly of FIG. 7 taken along section line 9-9 in FIG. 7.

As shown in FIGS. 7-9, the suture assembly 10 is loaded into the suturing device 28 and the needle 34 is placed in a retracted condition within the lumen of the catheter 30 (FIG. 7). For clarity, the needle thruster 44 is not shown in FIG. 7. The anchors 16, 18 of suture assembly 10 are slidably received within the lumen of the needle 34 such that the first anchor 16 is located forwardly of the second anchor 18. As described above, the sutures 12, 14 extend from the anchors 16, 18 through the elongated slot 42 in the needle 34 to the suture tensioner 22, which is located in front of the needle 34 in an end portion of the catheter 30.

In one illustrative embodiment, a spacer 54 is slidably received within the lumen of the needle 34. The spacer 54 is located between the first and second anchors 16, 18 of the suture assembly to maintain separation between the anchors and thereby limit inadvertent ejection of the second anchor 18 when the first anchor 16 is ejected from the needle 34 by the anchor ejector 48. The spacer may be fabricated from a digestible material, as would apparent to one of skill in the art, so that the spacer does not need to be removed by the surgeon during the surgical procedure. It is to be appreciated, however, that a spacer is not required and, if provided, it need not be made of a digestible material.

As shown in FIG. 8, the needle 34 of suturing device 28 may be moved to the deployed condition in which the needle 34 has been advanced by the needle thruster 44 to extend from the end of the catheter 30. The deployment of the needle 34 also results in the suture lock or tensioner 22 being driven from the catheter 30 because of its forward location with respect to the needle 34. The position of the first and second anchors 16, 18 relative to the needle 34, however, remains unchanged as the needle 34 is moved from the retracted condition to the deployed condition.

In one illustrative embodiment shown in FIGS. 10-14, the suturing device 28 may be used for placement of a suture assembly 10 on tissue or muscle within the gastrointestinal tract of a human patient. More particularly, the procedure is directed to endoscopic treatment of obesity by narrowing the pyloric sphincter of the patient by suturing and drawing portions of the pyloric muscle together so as to narrow the sphincter and reduce gastric emptying.

Figure 10:
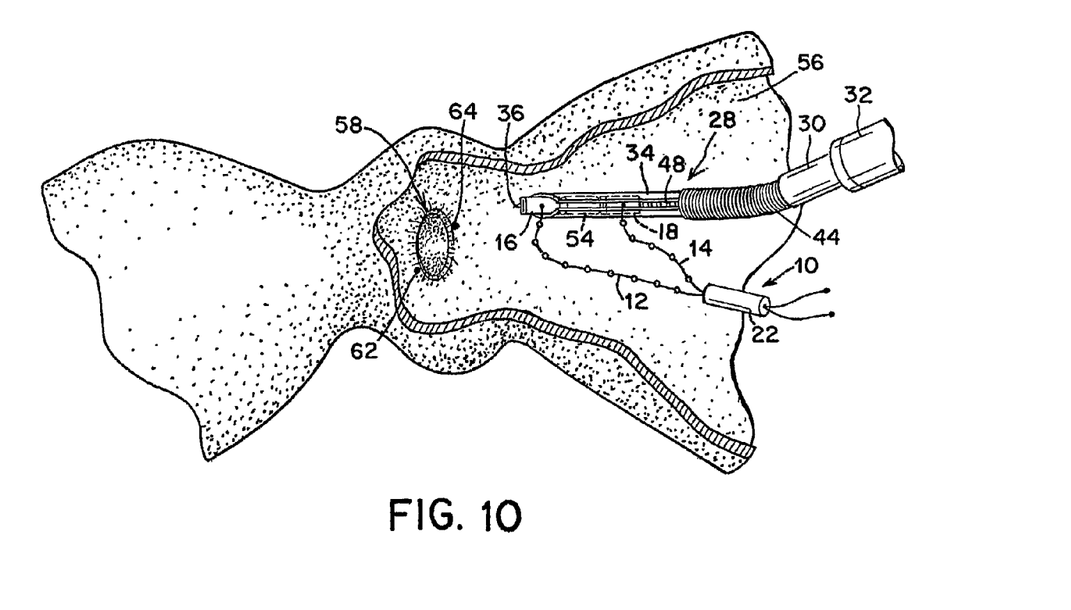
FIG. 10 is a partial perspective view of the apparatus and suture assembly of FIG. 7 within the gastrointestinal tract of an individual adjacent the pyloric junction with the apparatus and suture assembly enlarged from scale for clarity purposes.

As shown in FIG. 10, a suturing device 28 carrying a suture assembly 10 is inserted into the gastrointestinal tract 56 of an individual using an endoscope 32. The suturing device 28 and suture assembly 10 are shown enlarged from scale with respect to the gastrointestinal tract 56 to facilitate illustration. The suturing device 28 may be positioned adjacent to the pyloric sphincter 58 of the gastrointestinal tract 56 and the needle 34 may be deployed to extend from the catheter 30. As described further below, the sutures may be placed at first and second target locations 62, 64 of the pyloric muscle. However, it is to be understood that sutures may be placed at additional target locations, if desired.

Figure 11:
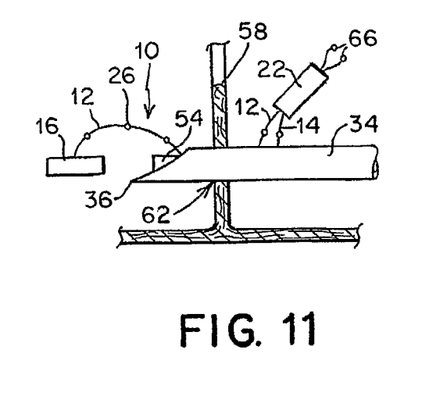
FIG. 11 is a partial side view of the apparatus and suture assembly of FIG. 10 with the needle piercing the gastrointestinal tract wall at a first location and the first lock bar ejected from the needle.

As shown in FIG. 11, the pyloric sphincter 58 is penetrated by the needle 34 at the first target location 62 such that the distal end 36 of needle 34 is located on the duodenum side of the gastrointestinal tract 56. With the needle 34 extending through the pyloric sphincter 58 at the first target location 62, the anchor ejector 48 of the suturing device 28 is advanced relative to the needle thruster 44. As a result, the anchors 16, 18 are slidingly advanced along the needle 34 through contact between second anchor 18 and the spring portion 52 of anchor ejector 48. As shown, the anchor ejector 48 is advanced by an amount sufficient to eject the first anchor 16 from the distal end 36 of needle 34 such that anchor 16 is located on the duodenum side of the gastrointestinal tract 56 at the first target location 62.

Figure 12:
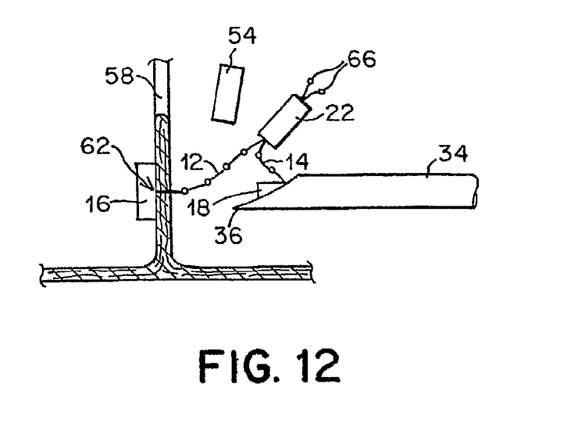
FIG. 12 is a partial side view of the apparatus and suture assembly of FIG. 11 with the needle withdrawn from the first location and the spacer ejected into the interior of the gastrointestinal tract.

As shown in FIG. 12, the needle 34 is then withdrawn from the pyloric muscle 58 at the first target location 62 such that the distal end 36 of needle 34 is returned to the gastric side of the gastrointestinal tract 56. The anchor ejector 48 may then be advanced relative to the needle thruster 44 by an amount sufficient to cause ejection of the spacer 54, if provided, from the needle 34 into the interior of the gastrointestinal tract 56.

Figure 13:
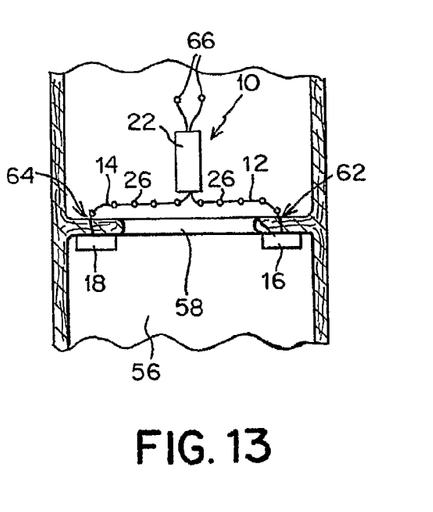
FIG. 13 is a partial side view of the gastrointestinal tract of FIGS. 11 and 12 with the first and second anchors of the suture assembly placed at first and second locations on the gastrointestinal tract wall and the suture tensioner in a retracted condition with respect to the sutures of the suture assembly.

As shown in FIG. 13, the anchoring procedure is repeated at the second target location 64 to penetrate the pyloric sphincter 58 with the needle 34 and eject the second anchor 18 on the duodenum side of the gastrointestinal tract 56. As shown, the placement of the anchors 16, 18 in the above-described manner anchors the first and second sutures 12, 14 at the first and second target locations 62, 64 through contact between the anchors 16, 18 and the pyloric muscle 58 which prevents the anchors 16, 18 from being pulled back through the pyloric muscle and into the gastric side of the gastrointestinal tract 56. As shown, the suture lock 22 is initially positioned in a retracted condition spaced away from the anchors and located adjacent the opposite ends 66 of the sutures 12, 14.

Figure 14:
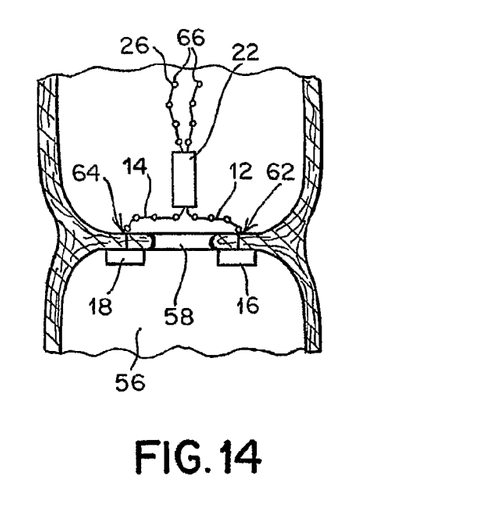
FIG. 14 is a partial side view of the gastrointestinal tract of FIG. 13 with the suture tensioner advanced along the sutures of the suture assembly to draw the first and second locations towards each other.

As shown in FIG. 14, with the sutures anchored at the target locations, the suture lock or tensioner 22 may then be advanced along the sutures 12, 14. This may be accomplished using suitable endoscopic grasping equipment (not shown), as apparent to one of skill in the art, to grip the suture lock 22 and the sutures 12, 14 adjacent the free ends 66 thereof. The suture lock 22 is then advanced along the sutures 12, 14 toward the anchors while the suture ends 66 are held in place. Advancement of the suture lock 22 along the sutures 12, 14 acts to cinch the sutures so as to draw portions of the pyloric sphincter 58 at the anchor locations 62, 64 towards each other due to the contact between the anchors 16, 18 and the pyloric muscle 58. Cinching the suture assembly in this manner to draw the pyloric muscle portions toward each other results in the narrowing of the pyloric sphincter, thereby providing reduced gastric emptying that may be beneficial for treating obesity. The amount of cinching applied to the suture assembly is determined by the surgeon to achieve a desired amount of narrowing of the pyloric sphincter.

If it is subsequently determined that the patient may benefit from a different rate of gastric emptying, it may be desirable to adjust the extent of narrowing of the pyloric sphincter. In this regard, a surgeon may readjust the suturing assembly in a manner that further narrows or enlarges the sphincter muscle to reduce or increase the amount of gastric emptying. This may be accomplished by repositioning the suture lock along the length of the sutures relative to one or both of the anchors.

Although use of the suture assembly and suturing device has been described in connection with endoscopic treatment of obesity involving narrowing and/or disabling the pyloric sphincter, it should be understood that the suture assembly and suturing device are not so limited and may be employed in other surgical procedures as would be apparent to one of skill in the art.

It should be understood that the foregoing description of various embodiments of the invention are intended merely to be illustrative thereof and that other embodiments, modifications, and equivalents of the invention are within the scope of the invention recited in the claims appended hereto.

What is claimed is:

1. An adjustable suture assembly, comprising:
a first suture and a first anchor attached to an end of the first suture, the first anchor constructed and arranged to anchor the first suture to tissue or muscle;
a second suture and a second anchor attached to an end of the second suture, the second anchor constructed and arranged to anchor the second suture to tissue or muscle; and
a suture lock slidable back and forth along the length of each of the sutures to adjustably secure the first and second sutures in a first secured position and subsequently in a second secured position;
wherein each of the first and second sutures includes a securement feature that engages the suture lock, and the securement feature on the first suture engages the securement feature on the second suture to inhibit movement therebetween.

2. The adjustable suture assembly according to claim 1, wherein in the first secured position, the first suture has a first length between the suture lock and the first anchor, wherein in the second secured position, the first suture has a second length between the suture lock and the first anchor and
wherein the second length is different than the first length so that the distance between the first and second anchors in the second secured position is different from the distance between the first and second anchors in the first secured position.

3. The adjustable suture assembly according to claim 2, wherein the second length is greater than the first length to loosen the suture assembly relative to the first secured position.

4. The adjustable suture assembly according to claim 2, wherein the second length is less than the first length to tighten the suture assembly relative to the first secured position.

5. The adjustable suture assembly according to claim 1, wherein each of the first and second anchors includes an elongated anchor body.

6. The adjustable suture assembly according to claim 5, wherein each of the first and second sutures is attached to the first and second anchors at an intermediate location between opposing ends of the elongated anchor body.

7. The adjustable suture assembly according to claim 1, wherein the suture lock is adjustably disposed along the first and second sutures.

8. The adjustable suture assembly according to claim 1, wherein the suture lock includes a passage and the first and second sutures extend through the passage.

9. The adjustable suture assembly according to claim 1, wherein the securement feature includes a plurality of projections spaced along the first and second sutures.

\* \* \* \* \*